US006388091B1

(12) United States Patent
Lee et al.

(10) Patent No.: US 6,388,091 B1
(45) Date of Patent: May 14, 2002

(54) PROCESS FOR THE PREPARATION OF 1,2,3, 9-TETRAHYDRO-9-METHYL-3-{(2-METHYL-1H-IMIDAZOL-1-YL)METHYL}-4H-CARBAZOL-4-ONE

(75) Inventors: Kwang-Ok Lee, Seongnam-si; Hee-Seock Kim, Daejeon; Young-Jin Ham; Maeng-Sup Kim, both of Seoul; Han-Kyeng Kim, Yongin-si; Cheol-Kyeung Kim, Namyangju-si; Kum-Sin Jung, Seoul; Hoe-Chul Lee, Seongnam-si; Ki-Eun Kim; Gwan-Sun Lee, both of Seoul, all of (KR)

(73) Assignee: Hanmi Pharm. Co., Ltd. (KR)

( * ) Notice: Subject to any disclaimer, the term of this patent is extended or adjusted under 35 U.S.C. 154(b) by 0 days.

(21) Appl. No.: 09/990,041

(22) Filed: Nov. 20, 2001

(30) Foreign Application Priority Data

Nov. 20, 2000 (KR) ......................................... 2000-68931
Jul. 11, 2001 (KR) ......................................... 2001-41524

(51) Int. Cl.$^7$ .............................................. C07D 233/58
(52) U.S. Cl. ..................................................... 548/311.4
(58) Field of Search ........................................ 548/311.4

(56) References Cited

U.S. PATENT DOCUMENTS 4,835,173 A * 5/1989 Tyers .......................... 514/397

* cited by examiner

*Primary Examiner*—Floyd D. Higel
*Assistant Examiner*—Andrea D. Small
(74) *Attorney, Agent, or Firm*—Anderson Kill & Olick, PC

(57) ABSTRACT

Pure -1,2,3,9-tetrahydro-9-methyl-3-[(2-methyl-1H-imidazol-1-yl)methyl]-4H-carbazol-4-one or a pharmaceutically acceptable salt thereof is prepared in a high yield by a simple process which reacts 1,2,3,9-tetrahydro-9-methyl-4H-carbazol-4-one with a 2-methylimidazole derivative in an organic solvent or in a mixture of an organic solvent and water in the presence of a halosilane compound.

9 Claims, No Drawings

PROCESS FOR THE PREPARATION OF 1,2,3, 9-TETRAHYDRO-9-METHYL-3-{(2-METHYL-1H-IMIDAZOL-1-YL)METHYL}-4H-CARBAZOL-4-ONE

FIELD OF THE INVENTION

The present invention relates to a method of preparing pure 1,2,3,9-tetrahydro-9-methyl-3-[(2-methyl-1H-imidazol-1-yl)methyl]-4H-carbazol-4-one and a pharmaceutically acceptable salt thereof in a high yield.

BACKGROUND OF THE INVENTION 1,2,3,9-tetrahydro-9-methyl-3-[(2-methyl-1H-imidazol-1-yl)methyl]-4H-carbazol-4-one of formula (I), which is used as an anti-vomiting agent due to its selective action on 5-HT$_3$ receptors, is prepared by various methods.

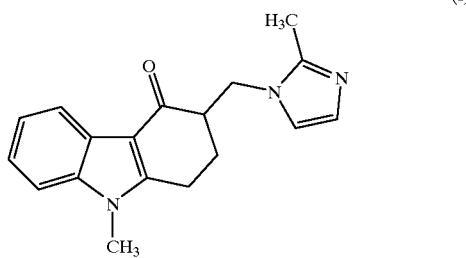

For example, Korean Patent Publication No. 92-1670 discloses a method of preparing the compound of formula (I) described in Scheme 1 and Korean Patent Publication No. 92-1671, a method illustrated in Scheme 2. However, these methods have the problem that the overall yield of the final product is very low, e.g., in the range of 4–9%.

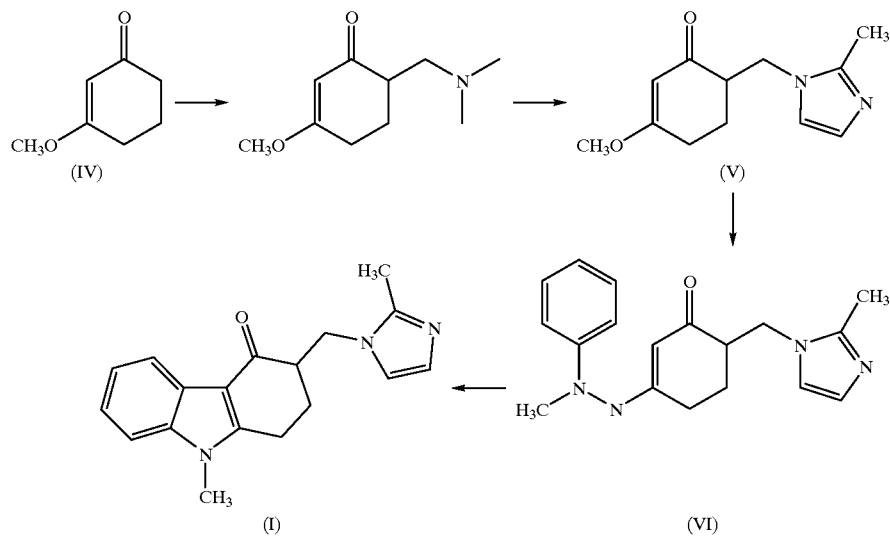

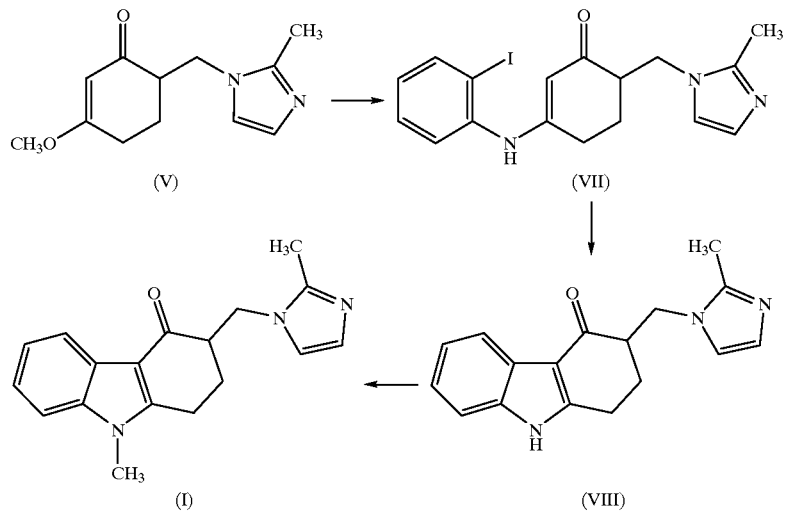

3

Although improved methods for preparing the subject compound are disclosed in Korean Patent Publication No. 92-3064 (Scheme 3) and in Korean Patent Publication Nos. 98-32228 and 98-32229 (Scheme 4), respectively, their overall yield of the compound of formula (I) is still low, i.e., about 60% or less.

Scheme 3

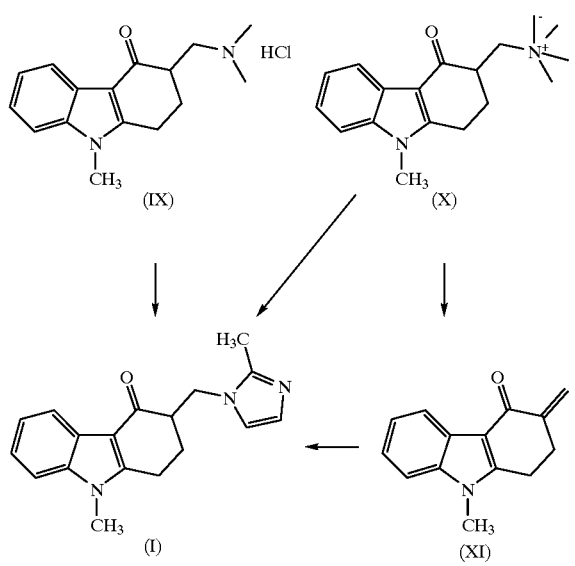

Scheme 4

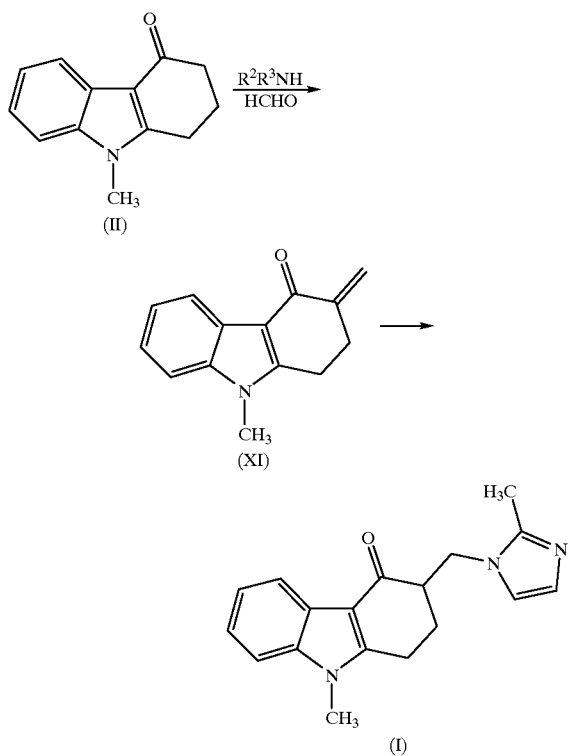

wherein $R^2$ and $R^3$ are each independently an alkyl group.

4

SUMMARY OF THE INVENTION

Accordingly, it is a primary object of the present invention to provide a simple, high-yield process for preparing 1,2,3,9-tetrahydro-9-methyl-3-[(2-methyl-1H-imidazol-1-yl)methyl]-4H-carbazol-4-one and a pharmaceutically acceptable salt thereof.

In accordance with one aspect of the present invention, there is provided a method of preparing the subject compound of formula (I), or a pharmaceutically acceptable salt thereof, which comprises reacting 1,2,3,9-tetrahydro-9-methyl-4H-carbazol-4-one (II) with a 2-methylimidazole derivative of formula (III) in an organic solvent or in a mixture of an organic solvent and water, in the presence of a halosilane compound:

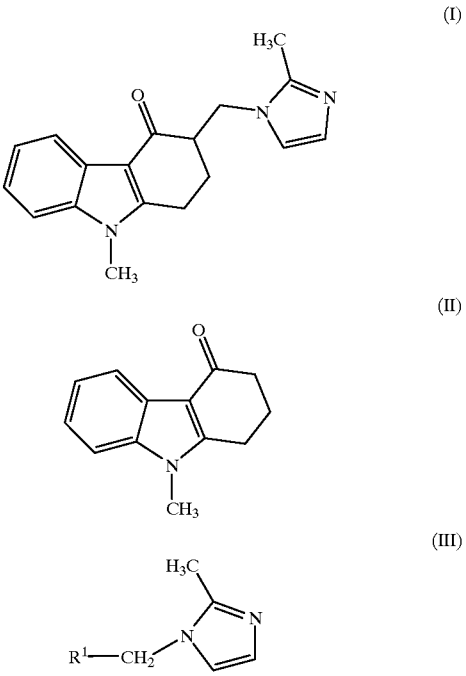

wherein $R^1$ is N,N-dimethylamino, N,N-diethylamino, N,N-dipropylamino, morpholin-4-yl, piperidin-1-yl or pirrolidin-1-yl.

DETAILED DESCRIPTION OF THE INVENTION 1,2,3,9-tetrahydro-9-methyl-4H-carbazol-4-one (II) may be prepared in accordance with the method disclosed in [*J. Org. Chem.*, 1980, 45, 2938] and [*J. Org. Chem.*, 1979, 44, 1236], and it is commercially available. Also, a 2-methylimidazole derivative of formula (III) may be prepared in accordance with the method disclosed in [*Tetrahedron Lett.*, 1990, 31(40), 5779] and [*J. Org. Chem.*, 1988, 53, 5685], representative examples thereof including 1-(N,N-dimethylaminomethyl)-2-methylimidazole, 1-(NN-diethylaminomethyl)-2-methylimidazole and 1-(N-morpholinyl)-2-methylimidazole.

In accordance with the present invention, the compound of formula (III) is employed in an amount ranging from 1 to 5 equivalents, preferably from 1 to 2 equivalents, based on the amount of the compound of formula (II).

Exemplary halosilane compounds which may be used in the inventive reaction include chlorotrimethylsilane, iodotrimethylsilane and t-butyldimethylchlorosilane, and the halosilane compound is used in an amount ranging from 0.5 to 5 equivalents, preferably from 1 to 3 equivalents, based on the amount of the compound of formula (II).

The inventive reaction may be performed at a temperature ranging from a room temperature to 150° C., preferably from 80 to 120° C., for a period ranging from 2 to 12 hours, preferably from 6 to 8 hours, in an organic solvent such as methylene chloride, chloroform, acetonitrile, tetrahydrofurane, 1,4-dioxane, toluene, N,N-dimethylformamide, ethanol and a mixture thereof, or in a mixture of one of the above organic solvents and water to induce precipitation of the product.

The reaction mixture is then cooled to room temperature. The crystals thus formed are filtered and washed with water, acetone, acetonitrile or isopropylalcohol, and dried, and the resulting product is recrystallized or purified by a conventional method to give a highly pure form of the compound of formula (I) in a high yield.

In addition, the above reaction mixture may be worked up to provide a pharmaceutically acceptable salt of the compound of formula (I). For example, a solvent such as acetone, acetonitrile and isopropylalcohol is added to the reaction mixture, and the resulting mixture is treated with hydrochloric acid to give hydrochloride dihydrate of the compound of formula (I); or an aqueous hydrochloric acid solution is added to the reaction mixture, and the resulting mixture is crystallized and purified by a conventional method to give hydrochloride of the compound of formula (I).

Optionally, 2-methylimidazole may be added to the reaction mixture to further improve the purity and yield of the desired compound. Said 2-methylimidazole is used in an amount ranging from 1 to 5 equivalents, preferably from 1 to 2 equivalents, based on the amount of the compound of formula (I).

The method of the present invention is very simple and provides a highly pure compound of formula (I) and a pharmaceutically acceptable salt thereof in a high yield.

The following Examples are given for the purpose of illustration only, and are not intended to limit the scope of the invention.

PREPARATION EXAMPLE 1

Preparation of 1-(N,N-Dimethylaminomethyl)-2-methylimidazole 20 g of 2-methylimidazole and 20 g of dimethylamine hydrochloride were dissolved in 50 ml of distilled water, and pH of the solution was adjusted to 5 with conc. hydrochloric acid. 22 g of 37% aqueous formaldehyde was added to the solution and kept at room temperature for 24 hrs. Then, the resulting solution was alkalized with 20% potassium hydroxide, saturated with potassium carbonate and extracted with chloroform. The organic layer was dried over potassium carbonate, and then vacuum-distilled, to obtain 28.1 g of the title compound (yield: 83%).

$^1$H-NMR (CDCl$_3$) δ: 2.27(s, 6H), 2.41(s, 3H), 4.45(s, 2H), 6.87(d, 2H).

PREPARATION EXAMPLE 2

Preparation of 1-(N,N-Diethylaminomethyl)-2-methylimidazole

The procedure of Preparation Example 1 was repeated except that 26.7 g of diethylamine hydrochloride was employed instead of dimethylamine hydrochloride, to obtain 31.4 g of the title compound (yield: 77%).

$^1$H-NMR (CDCl$_3$) δ: 1.11 (t, 6H), 2.40(s, 3H), 2.59(q, 4H), 4.42(s, 2H), 6.86(d, 2H).

PREPARATION EXAMPLE 3

Preparation of 1-(N-Morpholinylmethyl)-2-methylimidazole

The procedure of Preparation Example 1 was repeated except that 20 g of morpholine hydrochloride was employed instead of dimethylamine hydrochloride, to obtain 31 g of the title compound (yield: 70%).

$^1$H-NMR (CDCl$_3$) δ: 2.99(s, 3H), 2.49(t, 4H), 3.69(t, 4H), 4.47(s, 2H), 6.87(d, 2H).

EXAMPLE 1

Preparation of 12,3,9-Tetrahydro-9-methyl-3-[(2-methyl-1H-imidazol-1-yl)methyl]-4H-carbazol-4-one Hydrochloride Dihydrate 3.0 g of 1,2,3,9-tetrahydro-9-methyl-4H-carbazol-4-one and 2.4 g of 1-(N,N-dimethylaminomethyl)-2-methylimidazole obtained in Preparation Example 1 were suspended in 40 ml of acetonitrile, and 4.0 ml of chlorotrimethylsilane was added thereto. The suspension was heated to 110° C., and the reaction solvent was distilled off for 3 hrs. Then, 20 ml of acetonitrile was added thereto, and the reaction solvent was further distilled off for 3 hrs. The reaction mixture was cooled, and 30 ml of acetone and 2.8 ml of 6N hydrochloric acid were added thereto to induce crystallization of the product. The resulting crystals were filtered to obtain 4.12 g of the title compound (yield: 75%).

m.p.: 178–179° C.; $^1$H-NMR (DMSO-d$_6$) δ: 1.88~2.06 (m, 1H), 2.10~2.23(m, 1H), 2.65(s, 3H), 2.95~3.23(m, 3H), 3.74(s, 3H), 4.27(dd, 1H), 4.65(dd, 1H), 7.20(m, 2H), 7.56 (m, 2H), 7.67(d, 1H), 8.00(d, 1H); Elementary Analysis (as $C_{18}H_{19}N_3OHCl$. $2H_2O$); Measured value (%)—C:59.4, H:6.5, N:11.4; Calculated value (%)—C:59.1, H:6.6, N:11.5; Moisture (Calfisher): 10.1% (Calculated value: 9.85%); Purity (HPLC): 99%.

EXAMPLE 2

Preparation of 1,2,3,9-Tetrahydro-9-methyl-3-[(2-methyl-1H-imidazol-1-yl)methyl]-4H-carbazol-4-one Hydrochloride Dihydrate 3.0 g of 1,2,3,9-tetrahydro-9-methyl-4H-carbazol-4-one and 2.5 g of 1-(N,N-dimethylaminomethyl)-2-methylimidazole obtained in Preparation Example 1 were suspended in 30 ml of chloroform, and 3.8 ml of chlorotrimethylsilane was added thereto. The suspension was heated to 110° C., and the reaction solvent was distilled off for 3 hrs. Then, 30 ml of 1,4-dioxane was added thereto, and the reaction solvent was further distilled off for 3 hrs. The reaction mixture was cooled, and 30 ml of isopropanol and 2.6 ml of 6N hydrochloric acid were added thereto to induce s crystallization of the product. The resulting crystals were filtered to obtain 4.12 g of the title compound (yield: 75%).

The melting point and $^1$H-NMR data obtained were the same as those of Example 1.

Purity (HPLC): 99%.

EXAMPLE 3

Preparation of 1,2,3,9-Tetrahydro-9-methyl-3-[(2-methyl-1H-imidazol-1-yl)methyl]-4H-carbazol-4-one Hydrochloride Dihydrate 3.0 g of 1,2,3,9-tetrahydro-9-methyl-4H-carbazol-4-one and 2.1 g of 1-(N,N-dimethylaminomethyl)-2- methylimidazole obtained in Preparation Example 1 were suspended in 30 ml of chloroform, and 2.4 ml of chlorotrimethylsilane was added thereto. The suspension was heated to 90° C., and the reaction solvent was distilled off for 2 hrs. Then, 10 ml of 1,4-dioxane was added thereto and heated to 120° C., and the reaction solvent was further distilled off for 1 hr. 10 ml of 1,4-dioxane was added thereto and the reaction solvent was further distilled off for 1 hr. 50 ml of acetone was added to the reaction mixture, stirred at 60° C. for 30 minutes, and then at 20° C. for 2 hrs. The resulting crystals were filtered to obtain 3.4 g of crude 1,2,3,9-tetrahydro-9-methyl-3-[(2-methyl-1H-imidazol-1-yl)methyl]-4H-carbazol-4-one.

50 ml of acetone was added to the crude product and 2.2 ml of 6N HCl was slowly added thereto at 10° C. or below, stirred at the same temperature for 3 hrs, and filtered to obtain 4.02 g of the title compound (yield: 73%).

The melting point and $^1$H-NMR data obtained were the same as those of Example 1.

Purity (HPLC): 99%.

EXAMPLE 4

Preparation of 1 2,3,9-Tetrahydro-9-methyl-3-[(2-methyl-1H-imidazol-1-yl)methyl]-4H-carbazol-4-one Hydrochloride Dihydrate 3.0 g of 1,2,3,9-tetrahydro-9-methyl-4H-carbazol-4-one and 3.8 g of 1-(N-morpholinylmehyl)-2-methylimidazole obtained in Preparation Example 3 were suspended in 30 ml of chloroform, and 6.0 ml of t-butyldimethylchlorosilane was added thereto. The suspension was heated to 110° C., and the reaction solvent was distilled off for 3 hrs. Then, 20 ml of 1,4-dioxane was added thereto and the reaction solvent was further distilled off for 3 hrs. The reaction mixture was cooled and dissolved in 40 ml of chloroform, and the resulting solution was washed with 20 ml of saturated sodium bicarbonate. The organic layer was dried over magnesium sulfate and vacuum-distilled, to obtain 3.5 g of crude 1,2,3,9-tetrahydro-9-methyl-3-[(2-methyl-1H-imidazol-1-yl)methyl]-4H-carbazol-4-one.

The crude product was suspended in 40 ml of acetone and 2.4 ml of 6N HCl was slowly added thereto at 5° C. or below, stirred at the same temperature for 3 hrs, and filtered, to obtain 3.85 g of the title compound (yield: 70%).

The melting point and $^1$H-NMR data obtained were the same as those of Example 1.

Purity (HPLC): 99%.

EXAMPLE 5

Preparation of 1,2,3,9-Tetrahydro-9-methyl-3-[(2-methyl-1H-imidazol-1-yl)methyl]-4H-carbazol-4-one Hydrochloride Dihydrate 3.0 g of 1,2,3,9-tetrahydro-9-methyl-4H-carbazol-4-one and 2.4 g of 1-(N,N-dimethylaminomethyl)-2-methylimidazole obtained in Preparation Example 1 were suspended in 30 ml of chloroform, and 3.9 ml of chlorotrimethylsilane was added thereto. The suspension was heated to 110° C., and the reaction solvent was distilled off for 3 hrs. Then, 30 ml of chloroform was added thereto and the reaction solvent was further distilled off for 3 hrs. The reaction mixture was cooled and dissolved in 30 ml of chloroform, and the resulting solution was washed with 20 ml of saturated sodium bicarbonate. The organic layer was dried over magnesium sulfate and vacuum-distilled, to obtain 4.5 g of crude 1,2,3,9-tetrahydro-9-methyl-3-[(2-methyl-1H-imidazol-1-yl)methyl]-4H-carbazol-4-one.

The crude product was suspended in 30 ml of acetonitrile and 2.54 ml of 6N HCl was slowly added thereto at 10° C. or below, stirred at the same temperature for 3 hrs, and filtered, to obtain 4.07 g of the title compound (yield: 74%).

The melting point and $^1$H-NMR data obtained were the same as those of Example 1.

Purity (HPLC): 99%.

EXAMPLE 6

Preparation of 1,2,3,9-Tetrahydro-9-methyl-3-[(2-methyl-1H-imidazol-1-yl)methyl]-4H-carbazol-4-one Hydrochloride Dihydrate 3.0 g of 1,2,3,9-tetrahydro-9-methyl-4H-carbazol-4-one and 2.5 g of 1-(N,N-dimethylaminomethyl)-2-methylimidazole obtained in Preparation Example 1 were suspended in 30 ml of acetonitrile, and 3.8 ml of chlorotrimethylsilane was added thereto. The suspension was heated to 110° C., and the reaction solvent was distilled off for 3 hrs. Then, 30 ml of acetonitrile was added thereto and the reaction solvent was further distilled off for 2 hrs. The reaction mixture was subjected to column chromatography (eluent: chloroform/methanol=10/1) to obtain 3.62 g of 1,2,3,9-tetrahydro-9-methyl-3-[(2-methyl-1H-imidazol-1-yl)methyl]-4H-carbazol-4-one (yield: 82%).

The product was suspended in 30 ml of acetone and 3.0 ml of 6N HCl was slowly added thereto at 10° C. or below, stirred at the same temperature for 3 hrs, and filtered, to obtain 4.24 g of the title compound (yield: 77%).

The melting point and $^1$H-NMR data obtained were the same as those of Example 1.

Purity (HPLC): 99%.

EXAMPLE 7

Preparation of 1,2,3,9-Tetrahydro-9-methyl-3-[(2-methyl-1H-imidazol-1-yl)methyl]-4H-carbazol-4-one 3.0 g of 1,2,3,9-tetrahydro-9-methyl-4H-carbazol-4-one and 2.1 g of 1-(N,N-dimethylaminomethyl)-2-methylimidazole obtained in Preparation Example 1 were suspended in a mixture of 20 ml of chloroform and 20 ml of acetonitrile, and 3.8 ml of chlorotrimethylsilane was added thereto. The suspension was heated at 70° C. for 1 hr. Then, 2.5 g of 2-methylimidazole and 30 ml of water were added thereto and the reaction solvent was further distilled off at 100° C. for 6 hrs. The reaction mixture was cooled to room temperature, and the resulting crystals were filtered, and washed with water and then with acetone, to obtain 3.80 g of the title compound (yield: 86%).

$^1$H-NMR (CDCl$_3$) δ: 1.91~1.97(m, 1H), 2.19~2.21(m, 1H), 2.46(s, 3H), 2.84~3.02(m, 3H), 3.72(s, 3H), 4.07~4.15 (dd, 1H), 4.67~4.73(dd, 1H), 6.92~6.97(d, 2H), 7.29~7.36 (m, 3H), 8.26~8.29(m, 1H); Elementary Analysis (as C$_{18}$H$_{19}$N$_3$O); Measured value (%)—C:73.6, H:6.5, N:14.2; Calculated value (%)—C:73.7, H:6.5, N:14.3; Purity (BPLC): 99%.

EXAMPLE 8

Preparation of 1,2,3,9-Tetrahydro-9-methyl-3-[(2-methyl-1H-imidazol-1-yl)methyl]-4H-carbazol-4-one 3.0 g of 1,2,3,9-tetrahydro-9-methyl-4H-carbazol-4-one, 2.1 g of 1-(N,N-dimethylaminomethyl)-2-methylimidazole obtained in Preparation Example 1 and 2.5 g of 2-methylimidazole were suspended in 30 ml of chloroform, and 3.8 ml of chlorotrimethylsilane was added thereto. The suspension was heated at 70° C. for 1 hr. Then, 15 ml of acetonitrile and 30 ml of water were added thereto and the reaction solvent was further distilled off at 100° C. for 7 hrs. The reaction mixture was cooled to room temperature, and the resulting crystals were filtered, and washed with water and then with acetone, to obtain 3.76 g of the title compound (yield: 85%).

The melting point and $^1$H-NMR data obtained were the same as those of Example 7.

Purity (HPLC): 99%.

EXAMPLE 9

Preparation of 1,2,3,9-Tetrahydro-9-methyl-3-[(2-methyl-1H-imidazol-1-yl)methyl]-4H-carbazol-4-one 3.0 g of 1,2,3,9-tetrahydro-9-methyl-4H-carbazol-4-one, 2.7 g of 1-(N-morpholinylmethyl)-2-methylimidazole obtained in Preparation Example 3 and 2.5 g of 2-methylimidazole were suspended in a mixture of 25 ml of chloroform and 25 ml of acetonitrile, and 4.5 g of t-butyldimethylchlorosilane was added thereto. The suspension was heated at 70° C. for 1.5 hrs. Then, 30 ml of water were added thereto and the reaction solvent was further distilled off for 8 hrs. The reaction mixture was cooled to room temperature, and the resulting crystals were filtered, to obtain 3.58 g of the title compound (yield: 81%).

The melting point and $^1$H-NMR data obtained were the same as those of Example 7.

Purity (HPLC): 99%.

EXAMPLE 10

Preparation of 1,2,3,9-Tetrahydro-9-methyl-3-[(2-methyl-1H-imidazol-1-yl)methyl]-4H-carbazol-4-one Hydrochloride Dihydrate 3.0 g of 1,2,3,9-tetrahydro-9-methyl-4H-carbazol-4-one, 2.1 g of 1-(N,N-dimethylaminomethyl)-2-methylimidazole obtained in Preparation Example 1 and 2.5 g of 2-methylimidazole were suspended in a mixture of 15 ml of chloroform and 15 ml of acetonitrile, and 3.8 ml of chlorotrimethylsilane was added thereto. The suspension was heated at 70° C. for 1 hr. Then, 15 ml of water and 15 ml of 1,4-dioxane were added thereto and the reaction solvent was further distilled off for 6 hrs. The reaction mixture was cooled to room temperature, and the resulting crystals were filtered, to obtain 3.62 g of crude 1,2,3,9-tetrahydro-9-methyl-3-[(2-methyl-1H-imidazol-1-yl)methyl]-4H-carbazol-4-one.

The crude product was suspended in a mixture of 3 ml of water and 30 ml of ethanol, and 3.0 ml of 6N HCl was slowly added thereto at 10° C. or below, stirred at the same temperature for 3 hrs, and filtered, to obtain 4.29 g of the title compound (yield: 78%).

The melting point and $^1$H-NMR data obtained were the same as those of Example 1.

Purity (HPLC): 99%.

COMPARATIVE EXAMPLE

Method disclosed in Korean Patent Publication Nos. 98-32228 and 98-32229

Step 1) Preparation of 1,2,3,9-Tetrahydro-9-methyl-3-methylene-4H-carbazol-4-one 5 g of 1,2,3,9-tetrahydro-9-methyl-4H-carbazol-4-one was dissolved in 45 ml of glacial acetic acid, and 1.1 ml of morpholine was added thereto. While the mixture was refluxed with stirring, 3.4 g of paraformaldehyde was added to the mixture in three doses over 180 minutes. The reaction mixture was distilled under a reduced pressure to remove glacial acetic acid, and 150 ml of ethylacetate was added thereto. The organic layer was washed successively with saturated sodium bicarbonate, water, and then saturated saline, dried over magnesium sulfate and vacuum-distilled. The resulting residue was purified by column chromatography to obtain 6.9 g of the title compound.

Step 2) Preparation of 1,2,3,9-Tetrahydro-9-methyl-3-[(2-methyl- 1H-imidazol-1-yl)methyl]-4H-carbazol-4-one 3.0 g of the compound obtained in Step 1, 3.5 g of 2-methylimidazole and 10 g of alumina were mixed, and 70 ml of toluene was added thereto. The mixture was refluxed for 3 hrs with stirring. Chloroform was added to the reaction mixture, and filtered to remove alumina. The filtrate was washed with water and then with saturated saline. The organic layer was dried over magnesium sulfate and vacuum-distilled. The resulting residue was washed with a mixture of ethylacetate and hexane (1:1) to obtain 3.35 g of the title compound.

Step 3) Preparation of 1,2,3,9-Tetrahydro-9-methyl-3-[(2-methyl-1H-imidazol-1-yl)methyl]-4H-carbazol-4-one Hydrochloride Dihydrate 2 g of the compound obtained in Step 2 was dissolved in 80 ml of chloroform, and 28 ml of a chloroform solution of hydrochloric acid was added thereto. The resulting crystals was filtered and dried, to obtain 2.05 g of the title compound (overall yield from Step 1 to Step 3: 42.6%)

Purity (HPLC): 95%.

As shown above, the method of the present invention is simpler and gives a higher yield of pure 1,2,3,9-tetrahydro-9-methyl-3-[(2-methyl-1H-imidazol-1-yl)methyl]-4H-carbazol-4-one and a pharmaceutically acceptable salt thereof, as compared with the conventional method.

While exemplary embodiments of the subject invention have been described and illustrated, various changes and modifications may be made thereto without departing from the spirit of the present invention which should be limited only by the scope of the appended claims.

What is claimed is:

1. A method of preparing 1,2,3,9-tetrahydro-9-methyl-3-[(2-methyl-1H-imidazol-1-yl)methyl]-4H-carbazol-4-one of formula (I) or a pharmaceutically acceptable salt thereof which comprises reacting 1,2,3,9-tetrahydro-9-methyl-4H-carbazol-4-one of formula (II) with a 2-methylimidazole derivative of formula (III) in an organic solvent or in a mixture of an organic solvent and water, in the presence of a halosilane compound:

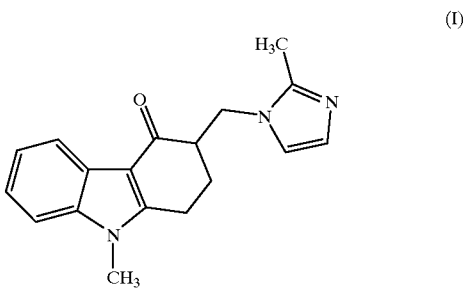

(I)

(II)

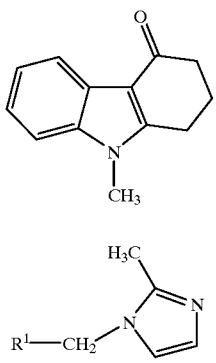

(III)

wherein R¹ is N,N-dimethylamino, N,N-diethylamino, N,N-dipropylamino, morpholin-4-yl, piperidin-1-yl or pirrolidin-1-yl.

2. The method of claim 1, wherein the reaction is carried out in the presence of 2-methylimidazole.

3. The method of claim 1, wherein the compound of formula (III) is 1-(N,N-dimethylaminomethyl)-2-methylimidazole, 1-(N,N-s diethylaminomethyl)-2-methylimidazole or 1-(N-morpholinyl)-2-methylimidazole.

4. The method of claim 1, wherein the compound of formula (III) is employed in an amount ranging from 1 to 5 equivalents based on the amount of the compound of formula (II).

5. The method of claim 1, wherein the halosilane compound is chlorotrimethylsilane, iodotrimethylsilane or t-butyldimethylchlorosilane.

6. The method of claim 1, wherein the halosilane compound is used in an amount ranging from 0.5 to 5 equivalents based on the amount of the compound of formula (II).

7. The method of claim 1, wherein the organic solvent is methylene chloride, chloroform, acetonitrile, tetrahydrofurane, 1,4-dioxane, toluene, N,N-dimethylformamide, ethanol or a mixture thereof.

8. The method of claim 1, wherein the reaction is performed at a temperature ranging from room temperature to 150° C.

9. The method of claim 1, wherein the reaction is performed for a period ranging from 2 to 12 hrs.

* * * * *